United States Patent [19]

Campbell

[11] Patent Number: 5,418,139
[45] Date of Patent: May 23, 1995

[54] METHOD FOR SCREENING FOR CARDIOMYOPATHY

[75] Inventor: Kevin P. Campbell, Iowa City, Iowa

[73] Assignee: University of Iowa Research Foundation, Iowa City, Iowa

[21] Appl. No.: 16,126

[22] Filed: Feb. 10, 1993

[51] Int. Cl.$^6$ .................. G01N 33/537; G01N 33/68; G01N 33/543

[52] U.S. Cl. .................................. 435/7.21; 435/960; 436/518; 436/172; 436/811; 436/536

[58] Field of Search ............... 435/7.21, 960; 436/518, 436/536, 172, 811

[56] References Cited

U.S. PATENT DOCUMENTS 5,187,063 2/1993 Campbell ........................... 435/7.21

OTHER PUBLICATIONS

Geisterfer-Lowrance, et al., "A Molecular Basis for Familial Hypertrophic Cardiomyopathy: A β Cardiac Myosin Heavy Chain Gene Missense Mutation", *Cell* 62:999–1006, (1990).

Nigro, et al., "The Incidence and Evolution of Cardiomyopathy in Duchenne Muscular Dystrophy", *International Journal of Cardiology* 26:271–277, (1990).

Anan, et al., "Myocardial Patchy Staining of Dystrophin in Becker's Muscular Dystrophy Associated With Cardiomyopathy", *American Heart Journal* 123:1088–1089 (1992).

Roberds, S. L. et al *J. Biol. Chem.* 268(16):11496 Jun. 5 1993.

Byers, T. J. et al *J. Cell Biol.* 115(2):411 Oct. 1991.

Valetine, B. A. et al *Am. J. Pathol.* 135(4):671 Oct. 1989.

*Primary Examiner*—Toni R. Scheiner
*Assistant Examiner*—Nancy J. Parsons
*Attorney, Agent, or Firm*—Kevin M. Farrell

[57] ABSTRACT

Disclosed herein are methods for screening for primary cardiomyopathy. The methods are preferably immunological methods in which the level of binding of a monoclonal or polyclonal antibody to a 50 kD glycoprotein component of a mammalian muscle tissue is determined. This level of binding is compared to the level of binding observed when non-dystrophic tissue is treated in an otherwise identical manner. A substantial reduction in the level of binding to the 50 kD glycoprotein in the experimental mammalian muscle tissue has been determined to be a screen for primary cardiomyopathy.

10 Claims, No Drawings

METHOD FOR SCREENING FOR CARDIOMYOPATHY

BACKGROUND OF THE INVENTION

Cardiomyopathy is a generic term used to describe conditions in which lesions develop in the myocardium of the heart. The disease may be classified as secondary or primary. The secondary cardiomyopathies are those which are associated with an identifiable disease condition. Primary cardiomyopathy is a diagnosis which is made only after all known causes have been considered and eliminated. Primary cardiomyopathy is the most common form of the disease in Western countries.

In general, there are three clinical classifications of primary cardiomyopathy: dilated (congestive), restrictive and hypertrophic. Dilated cardiomyopathy is characterized by the dysfunction of left and/or right ventricular function. This condition leads to cardiac enlargement. Restrictive cardiomyopathy is characterized by abnormal diastolic function associated with excessively rigid ventricular walls. Hypertrophic cardiomyopathy is characterized by left ventricular hypertrophy.

Present methods available for the evaluation of the cardiomyopathies include chest roentgenogram, electrocardiogram, echocardiogram, radionuclide studies and cardiac catheterization. Although the characterization of the cardiomyopathies on the basis of clinical presentation is useful, a method that would enable an etiologic diagnosis is preferable. In many cases, such a diagnosis is not possible.

SUMMARY OF THE INVENTION

The subject invention relates to methods for detecting primary cardiomyopathy by immunological techniques. These methods are based on the discovery of a substantial reduction in the levels of a dystrophin-associated glycoprotein in mammalian muscle tissue samples from a cardiomyopathy animal model and from a human patient.

Preferred methods for detecting levels of dystrophin-associated proteins are immunological methods. Particularly useful methods are fluorescence microscopy and immunoblot techniques. Such methods enable an etiologic diagnosis for cardiomyopathy and are preferable to the current characterization on the basis of clinical presentation.

DETAILED DESCRIPTION OF THE INVENTION

It has been reported that a set of proteins are tightly associated with dystrophin in vivo. These include, for example a dystrophin-associated protein having a molecular weight of 59 kD (59-DAP), and four dystrophin-associated glycoproteins having the molecular weights 35 kD (35-DAG), 43 kD (43-DAG), 50 kD (50-DAG) and 156 kD (156-DAG). Antibodies specifically reactive with these antigens have been identified.

It has been demonstrated that a substantial reduction in the level of dystrophin and/or dystrophin-associated proteins correlates with the muscular dystrophy phenotype (particularly with respect to Becker's or Duchenne's muscular dystrophy). Based on this observation, it was of interest to determine whether a reduction in the level of these proteins could be correlated with another disease classification which is characterized by muscle cell necrosis. More specifically, it was of interest to determine whether the appearance of primary cardiomyopathy could be correlated with a substantial reduction in dystrophin and/or the dystrophin-associated proteins.

The subject invention in based on the discovery of substantial reduction in the levels the 50-DAG in muscle tissue from an animal model and from a human patient afflicted with primary cardiomyopathy. In addition to the 50-DAG, preliminary evidence suggests that the levels of other dystrophin-associated proteins are also affected.

The invention relates to a method for diagnosing primary cardiomyopathy. A muscle tissue biopsy sample is obtained from the mammal for analysis according to the methods described herein. Preferred muscle tissue biopsy samples are obtained from cardiac or skeletal muscle tissue. Biopsy samples can be obtained using a variety of methods including, for example, the use of a biopsy needle. The muscle tissue is analyzed for substantially reduced levels of the 50-DAG.

Substantial reduction, as used herein, refers to a reduction in the level of the 50-DAG in experimental tissue of at least about 50% relative to the level of the 50-DAG in non-cardiomyopathic tissue. Quantitative methods for monitoring levels of dystrophin-associated protein have been previously reported (see e.g., Ervasti et al., Nature 345:315–319 (1990).

Analysis of the levels of dystrophin-associated proteins in the muscle tissue sample is best carried out by immunological methods. Monoclonal or polyclonal antibodies which bind specifically to dystrophin-associated proteins are contacted with the muscle tissue biopsy sample under conditions appropriate for the binding of antibody to antigen. Particularly useful for this analysis are affinity purified polyclonal antibodies.

Antibodies specific for the various components of the dystrophin-glycoprotein complex are prepared by conventional methods. Methods for isolating the dystrophin-glycoprotein complex have been previously reported. For example, the dystrophin-glycoprotein complex can be isolated from detergent solubilized skeletal muscle membranes using affinity chromatography and density gradient ultracentrifugation. Lectins are proteins or glycoproteins which bind certain sugars or oligosaccharides. This property can be used to isolate certain glycoproteins from a complex mixture and is extremely useful as a general approach to the purification of membrane proteins, many of which are glycosylated. In the present invention, the linked components of the dystrophin-glycoprotein complex can be isolated as an intact complex with lectins that bind to the glycoprotein components of the complex. The lectins are typically coupled to a solid support such as a chromotographic gel (i.e., sepharose, agarose, etc.) and a complex mixture of membrane components is passed through a chromatography column containing the gel with bound lectin. The glycoproteins of membrane components bind to the lectin while the other components of the mixture pass through the column. A variety of lectins can be used in affinity-based methodologies to isolate the dystrophin-glycoprotein complex.

The dystrophin-glycoprotein complex can be further purified using density gradient ultracentrifugation. The eluate from the affinity column as described above is applied as a narrow band to the top of a solution in a centrifuge tube. To stabilize the sedimenting components of the eluate against convection mixing, the solution beneath the band contains an increasingly dense solution of an inert, highly soluble material such as sucrose (a density gradient). Under these conditions, the different fractions of the eluate sediment at different rates forming distinct bands that can be individually collected. The rate at which each component sediments depends on its size and shape and is normally expressed as its sedimentation coefficient or S value. Using this technique, the size of the dystrophin-glycoprotein complex was estimated to be approximately 18 S by comparing its migration to that of standards of varying size.

Another form of affinity chromatography which can be used to isolate the dystrophin-glycoprotein complex is known as immunoaffinity purification. This technique utilizes the unique high specificity of polyclonal and monoclonal antibodies as well as selected lectins. Such highly specific molecules are extremely valuable tools for rapid, selective purification of antigens. In principle, the antigen is coupled (immobilized) on a column support and this is used to selectively adsorb antigen from a mixture containing many other antigens. The antigens for which the antibody has no affinity can be washed away, and the purified antigen then eluted from the bound antibody or lectin with an elution buffer. The separation and isolation of the components of the dystrophin-glycoprotein complex can be accomplished by conventional techniques such as SDS-polyacrylamide gel electrophoresis (SDS-PAGE) or gel filtration high pressure liquid chromotography.

Monoclonal and polyclonal antibodies specific for non-dystrophin components of the dystrophin glycoprotein complex are prepared by conventional methods. Monoclonal antibodies can be prepared, for example, by immunizing an animal with a preparation containing the dystrophin-glycoprotein complex. A fused cell hybrid is then formed between antibody-producing cells from the immunized animal and an immortalizing cell such as a myeloma to produce a hybridoma. The hybridomas are then screened for production of anti-non-dystrophin component antibodies using standard immunological techniques.

Polyclonal antibodies can be prepared by immunizing an animal with a crude preparation of the dystrophin-glycoprotein complex or the purified non-dystrophin components of the complex. The animal is maintained under conditions whereby antibodies reactive with the components of the complex are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG or IgM). Additionally, polyclonal antibodies can be affinity purified to generate a polyclonal antibody preparation which is antigen specific. This is best accomplished by attaching a purified component of the dystrophin-glycoprotein complex to a solid support and preparing an affinity column.

As shown in the Exemplification section which follows, it has been determined that a reduction in the extent of antibody binding to the 50-DAG correlates with primary cardiomyopathy. A diagnostic method for the detection of cardiomyopathy can be carried out in a variety of formats.

In the preferred embodiment of the diagnostic method of the invention, a muscle biopsy sample is treated in a procedure which renders the non-dystrophin components available for complexing with antibodies directed against said components. Muscle biopsy samples can be taken from any muscle; preferably cardiac or skeletal muscle. The amount of muscle obtained should be enough to extract the components of the dystrophin-glycoprotein complex from muscle membranes and detect their presence by the diagnostic methods described within this application. Alternative methods of extraction can be used.

For biopsy samples greater than 500 mg, the muscle tissue can be homogenized by mechanical disruption using apparatus such as a hand operated or motor driven glass homogenizer, a Waring blade blender homogenizer, or an ultrasonic probe. Homogenization can occur in a buffer comprising 20 mM sodium pyrophosphate, 20 mM sodium phosphate monohydrate, 1 mM magnesium chloride, 0.303M sucrose,, 0.5 mM EDTA, pH 7.1, with various protease inhibitors such as aprotinin (0.5 $\mu$g/ml), benzamidine (100 $\mu$g/ml), iodoacetamide (185 $\mu$g/ml), leupeptin (0.5 $\mu$g/ml), pepstatin A (0.5 $\mu$g/ml) and PMSF (40 $\mu$g/ml). Heavy microsomes can be prepared from homogenized skeletal muscle by the method of Mittchel, et al., *J. of Cell Biol*, 95: 1008–1016 (1983). The microsomes are then washed with a physiological salt solution and solubilized in saline containing detergent and protease inhibitors. Following solubilization of the microsomes, the sample is treated with sodium SDS. In the present case, SDS acts to dissociate the linked components of the dystrophin-glycoprotein complex, thereby allowing their separation.

For muscle biopsy samples less than 500 mg, an alternative extraction procedure can be used. Samples are frozen in liquid nitrogen and crushed using a mortar and pestle and prepared for electrophoresis by treatment with SDS as described by Hoffman et al., (*N. Eng. J. of Med.* 318:1363–1368 (1988)).

The SDS treated sample is then electrophoresed by polyacrylamide gel electrophoresis (PAGE). Following separation by SDS-PAGE, the separated components of the dystrophin-glycoprotein complex are transferred from the gel matrix to a solid support to generate a protein transfer blot.

Alternatively, tissue specimens (e.g., human biopsy samples) can be tested for the presence of the components of the dystrophin-glycoprotein complex by using monoclonal or polyclonal antibodies in an immunohistochemical technique, such as the immunoperoxidase staining procedure. In addition, immunofluorescent techniques can be used to examine human tissue specimens. In a typical protocol, slides containing cryostat sections of frozen, unfixed tissue biopsy samples are air dried and then incubated with the anti-non-dystrophin component antibody preparation in a humidified chamber at room temperature. The slides are layered with a preparation of fluorescently labeled antibody directed against the monoclonal antibody. The staining pattern and intensities within the sample are determined by fluorescent light microscopy.

The antibodies of the present invention can also be used in an enzyme-linked immunoadsorbant assay (ELISA) for determining the absence or presence of non-dystrophin components of the dystrophin-glycoprotein complex. Antibodies against non-dystrophin components to be measured are adsorbed to a solid support, in most cases a polystyrene microtiter plate. After coating the support with antibody and washing, a solubilized sample is added. If a non-dystrophin component is present for which the antibodies are specific, they will bind to the adsorbed antibodies. Next, a conjugate that will also bind to the non-dystrophin component is added. Conjugates are secondary antibody molecules to which an enzyme is covalently bound. After addition of a chromogenic substrate for the enzyme, the intensity of the colored reaction products generated will be proportional to the amount of the non-dystrophin component present, determination of the intensity of the color produced by a standard series of non-dystrophin component concentrations will allow the calculation of the amount of non-dystrophin component in an unknown sample. Many variations of this assay exist as described in Voller, A., Bidwell, D. E. and Bartlett, A., The Enzyme Linked Immunosorbent Assay (ELISA): A guide with abstracts of microplate applications, Dynatech Laboratories, Alexandria, Va. (1979) and are hereby incorporated by reference.

The invention is now further and specifically illustrated by the following examples. All parts and percentages are by weight unless otherwise specified.

EXAMPLES

Example 1

The inbred Syrian hamster strain Bio-14.6 is an established animal model for cardiomyopathy, characterized by muscle cell necrosis and hypertrophy, ultimately leading to congestive heart failure. In this Example, the status of the individual components of the dystrophin-glycoprotein complex in muscle tissue from control and cardiomyopathic hamsters is compared with that of the mdx mouse, an animal model for Duchenne muscular dystrophy.

Isolation of Cardiac and Skeletal Muscle Membranes

Total cardiac and skeletal muscle membranes were prepared from age-matched control hamsters and cardiomyopathic Syrian hamsters, as well as control and mdx mice. Control hamster strain F1B and cardiomyopathic hamster strain Bio-14.6 were obtained from Biobreeders, Watertown, Mass. Hind leg and back muscle were dissected and homogenized in 7.5 volumes of homogenization buffer (20 mM sodium pyrophosphate, 20 mM sodium phosphate monohydrate, 1 mMMgCl$_2$, 0.303M sucrose, 0.5 mM EDTA, (pH 7.0)) by a Polytron PTS-10-S (Kinematic. GmbH, Luzern, Switzerland) in the presence of a protease inhibitor cocktail. Homogenates were centrifuged for 15 minutes at 1100×g, the supernatant filtered through 4 layers of cheese cloth and total membranes obtained by a final centrifugation for 37 minutes at 140,000×g. Protein was determined by conventional methods using bovine serum albumin as a standard.

Antibodies

Affinity-purified sheep antibodies to the individual components of the dystrophin-glycoprotein complex were produced and characterized as described by Ohlendieck and Campbell (J. Cell Biol. 115:1685–1694 (1991)). Antibodies against the dystrophin-associated proteins of 35-DAG, 43-DAG, 50-DAG, 59-DAP and 156-DAG are highly specific for their respective antigen and do not immunologically cross-react with each other. In addition, the following monoclonal antibodies were used in this study: mAb VIA4$_2$ to dystrophin, mAb IIH6 to dystrophin-associated glycoprotein of 156-DAG, mAb IID8 to cardiac sarcoplasmic reticulum Ca$^{2+}$-ATPase of fast-twitch skeletal muscle, mAb VIID1$_2$ to calsequestrin, mAb IIID5 to $\alpha_1$-subunit of dihydropyridine receptor, mAb McB2 to Na/K-ATPase, and mAb RyR-1 to cardiac ryanodine receptor. Each of these antibodies have been described in printed publications. Polyclonal antibodies to skeletal muscle ryanodine receptor were raised in sheep and rabbit antibodies against the unique C-terminal sequences of human dystrophin and human dystrophin-related protein were affinity-purified and characterized.

Results

Immunolocalization of components of the dystrophin-glycoprotein complex in skeletal and cardiac muscle from normal and cardiomyopathic Syrian hamsters Transverse skeletal muscle cryosections from six-week-old FiB (Control) or BIO 14.6 cardiomyopathic (CMH) hamsters were stained with hematoxylin and eosin. Hematoxylin and eosin staining of frozen cross-sections of cardiomyopathic hamster (CMH) skeletal muscle revealed muscle fibers of various sizes with rounded contours and central nucleation. Central nucleation is characteristic of muscle cell regeneration.

Additional cryosections were labeled by indirect immunofluorescence (see e.g., Zubrzycka-Gaarn et al., Nature 333:466–469 (1988) and Ohlendieck et al., J. Cell. Biol. 122:135–148 (1991)) with affinity-purified antibodies against the C-terminus of dystrophin (DYS) or against the dystrophin-associated proteins 156-DAG, 59-DAP, 50-DAG, 43-DAG and 35-DAG. 50-DAG antibodies were affinity-purified against the entire protein or against a 50-DAG peptide as described by Noorgard et al. (J. Mol. Cell. Cardiol. 19:589–594 (1987)). Antibody binding was detected using a biotinylated secondary antibody (Vector Laboratories) and fluorescein-conjugated streptavidin (Jackson ImmunoResearch Laboratories). Sections from control and cardiomyopathic hamsters were placed on the same microscopy slide to ensure identical treatment, and photographs were processed using identical times and conditions for a given antibody on both control and cardiomyopathic sections. Indistinguishable results were observed using skeletal muscle obtained from 2- to 24-week-old hamsters.

All DAGs were localized at the cell periphery of hamster skeletal muscle, consistent with their localization in mouse and rabbit. The 59-kDa dystrophin-associated protein (59-DAP) and the 156- and 43-kDa DAGs (156-DAG and 43-DAG) were present at apparently equal levels in normal and CMH muscle as determined by immunofluorescence, whereas the 35-kDa DAG (35-DAG) was slightly decreased at the CMH sarcolemma. However, the 50-kDa DAG (50-DAG) was not detected by immunofluorescence in CMH muscle using either of two affinity-purified antibodies against this protein. Identical results were obtained using tissue from hamsters ranging from 2 to 24 weeks of age. Thus, 50-DAG was undetectable before, during, and after the age of primary cardiac necrosis.

Immunohistochemical analysis of cardiac cryosections

Immunohistochemical analysis of cardiac cryosections was performed to determine levels of dystrophin and DAPs in normal and CMH cardiac sarcolemma. Cardiac ventricle cryosections from 19-week-old FIB (control) or BIO 14.6 cardiomyopathic (CMH) hamsters were labeled by indirect immunofluorescence with affinity-purified antibodies against the C-terminus of dystrophin (DYS) or the DAGs as described above.

All components of the dystrophin-glycoprotein complex were clearly localized to normal hamster cardiac sarcolemma. Also, staining of small processes leading inward from the sarcolemma was consistent with the presence of these proteins in hamster cardiac T-tubules as has been observed in rabbit cardiac muscle. Dystrophin and 59-DAP were present at nearly equal levels in normal and CMH cardiac membranes. 35-DAG staining was also lower in CMH membranes, and 50-DAG was not detected in CMH heart. In contrast to the findings in skeletal muscle, 156-DAG and 43-DAG appeared decreased in CMH cardiac sarcolemma relative to that of normal hamsters. Thus, DAGs appear to be more deficient in CMH cardiac muscle than in CMH skeletal muscle. This may explain why the cardiomyopathic hamsters experience more severe cardiac symptoms than skeletal muscle symptoms.

Immunoblot analysis of muscle tissue homogenates

To more accurately quantify the abundance of dystrophin and DAGs in the BIO 14.6 hamster, immunoblot analysis was performed on skeletal muscle and cardiac homogenates. Tissue homogenates were prepared from control hamsters and cardiomyopathic Syrian hamsters as described previously (Ohlendieck et al., *J. Cell Biol.* 112:135–148 (1991)). Proteins were fractionated on 3–12% gradient SDS-polyacrylamide gels. Transfer of proteins to nitrocellulose was performed according to Towbin et al. (*J. Natl. Acad. Sci. USA* 76:4350–4354 (1979)), and immunoblot staining with antibodies was performed as previously described (Campbell and Kahl, *Nature* 338:259–262 (1989)). Blots were stained with monoclonal antibody McB2 against the Na/K-ATPase, an affinity-purified rabbit antibody against the C-terminal of dystrophin (DYS), monoclonal antibody IIH6 against the 156DAG, or a mixture of affinity-purified antibodies against the 35-, 43-, 50-, and 59-kDa DAPs (DAPs).

Control experiments were performed on immunoblots of homogenates to demonstrate that any changes in protein levels between normal and cardiomyopathic hamsters were not due to nonspecific degradation of membrane proteins. The pattern of binding of wheat germ agglutinin, concanavalin A, and jacalin to CMH skeletal muscle and cardiac homogenates was unaffected, indicating that any changes in DAG levels were specific rather than due to general effects in necrotic tissue. Additionally, integral membrane proteins involved in excitation-contraction coupling specifically the ryanodine receptor, dihydropyridine receptor, and $Ca^{2+}$-ATPase were present at comparable levels in both control and CMH skeletal muscle and cardiac homogenates. These results indicate that the majority of integral membrane proteins and glycoproteins are unaffected in cardiomyopathic hamster skeletal muscle and heart. Furthermore, the equal density of Na/K-ATPase in control and cardiomyopathic hamster skeletal muscle and heart demonstrates that homogenates from both strains contain equal amounts of sarcolemma.

In skeletal muscle, dystrophin, 156-DAG, and 59-DAP were present at approximately equal levels in control and cardiomyopathic hamsters. 43-DAG and 35-DAG were present at lower levels in CMH skeletal muscle relative to that of controls. However, 50-DAG was undetectable on immunoblots of skeletal muscle homogenates from cardiomyopathic hamsters. In heart, as in skeletal muscle, dystrophin and 59-DAP were present at equal levels in normal and cardiomyopathic hamsters, whereas 43-DAG and 35-DAG were reduced in CMH heart relative to normal heart. 50-DAG was also undetected on immunoblots of BIO 14.6 cardiac homogenates. However, 156-DAG was greatly reduced in CMH heart. It remains to be determined why 156-DAG is deficient in CMH heart but not skeletal muscle although both tissues are affected by the disease.

Skeletal and cardiac myocytes of cardiomyopathic hamsters contain elevated levels of intracellular calcium. Increased levels of dihydropyridine receptors and ryanodine receptors have been reported in CMH cardiac membranes but not in cardiac homogenates. Using immunoblot analysis no differences were observed between normal and CMH skeletal muscle or heart in levels of $Na+/K+$-ATPase, dihydropyridine receptor, ryanodine receptor, or $Ca^{2+}$-ATPase.

Immunoblot analysis of components of the dystrophin-glycoprotein complex in cardiac muscle membranes of normal and mdx mice The mdx mouse does not experience cardiac symptoms or histopathological changes in cardiac muscle. However, all DAGs are greatly reduced in cryosections and total membranes of mdx mouse skeletal muscle. Here immunoblot analysis was used to determine the status of DAGs in dystrophin-deficient, histologically normal mdx heart. Immunoblots from control and mdx murine cardiac tissue were stained with monoclonal antibody McB2 against the Na/K-ATPase, an affinity-purified rabbit antibody against the C-terminal of dystrophin (DYS), monoclonal antibody IIH6 against the 156-DAG, or a mixture of affinity-purified antibodies against the 35-, 43-, 50-, and 59-kDa DAPs (DAPs).

The 156-, 50-, 43-, and 35-kDa DAGs were present at approximately normal levels in mdx cardiac membranes, but the 59-kDa DAP was greatly reduced. Identical results were obtained using mice ranging in age from 5 to 55 weeks. The specific loss of 59-DAP is consistent with its direct association with dystrophin as has been previously proposed. The remaining DAGs are preserved in cardiac sarcolemma, presumably by interacting with dystrophin-related protein (DRP), an autosomal homolog of dystrophin that is present in cardiac myocytes of mdx mice. DRP expression is absent from cardiac muscle of normal mice. Thus, mdx mice may be relatively free of cardiomyopathies due to the ability of DRP to compensate for the loss of dystrophin by associating with membrane-spanning DAGs to preserve the link between cytoskeleton and extracellular matrix.

This work demonstrates that the 50-kDa DAG is deficient in skeletal muscle and heart of the BIO 14.6 cardiomyopathic hamster, although dystrophin is present at normal levels and at its normal subcellular location.

Example 2

To determine whether human cardiomyopathic tissue would mimic the protein distribution pattern described above in connection with the animal model system, immunoblots were prepared from human cardiac tissue. The tissue samples were obtained from a patient diagnosed with primary cardiomyopathy and from an unaffected control patient. The immunoblot preparation, staining and analysis was carried out as described above. These experiments demonstrated a substantial reduction in the level of the 50-DAG in the cardiomyopathic tissue when compared to the control tissue. As was observed in the animal model system, reduction in other dystrophin-associated proteins was also observed. The significance of the reduction in the levels of dystrophin-associated proteins other than the 50-DAG remains to be investigated.

Equivalents

Those skilled in the art will know, or be able to ascertain using no more than routine experimentation, many equivalents to the specific embodiments of the invention described herein. These and all other equivalents are intended to be encompassed by the following claims.

I claim:

1. A method for screening for primary cardiomyopathy in a mammal comprising the steps of:
   a) providing a muscle tissue sample from the mammal;
   b) contacting the muscle tissue sample, or a component thereof, with an antibody which binds to a dystrophin-associated glycoprotein having a molecular weight of about 50 kD, under conditions appropriate for binding;
   c) detecting the level of binding of the antibody to the 50 kD dystrophin-associated glycoprotein from the muscle tissue;
   d) comparing the level of binding of the antibody to the 50 kD dystrophin-associated glycoprotein from the muscle tissue, to the level of binding of the antibody to the 50 kD dystrophin-associated glycoprotein in a normal control muscle tissue, a substantial reduction in the level of binding in the tissue, as compared to control tissue, being indicative of primary cardiomyopathy.

2. A method of claim 1 wherein the experimental muscle tissue sample is a skeletal muscle tissue sample or a cardiac muscle tissue sample.

3. A method of claim 2 wherein the mammal is a human.

4. A method for screening for primary congestive cardiomyopathy in a mammal comprising the steps of:
   a) providing a cardiac muscle tissue biopsy sample suitable for histochemical analysis;
   b) contacting the cardiac muscle tissue biopsy sample with an antibody which binds to a dystrophin-associated glycoprotein having a molecular weight of about 50 kD;
   c) washing the cardiac muscle tissue biopsy sample to remove non-specifically bound antibody;
   d) detecting the level of binding of the antibody specific for the 50 kD dystrophin-associated glycoprotein from the cardiac muscle tissue biopsy sample; and
   e) comparing the level of binding of the antibody to the 50 kD dystrophin-associated glycoprotein from the cardiac muscle tissue biopsy sample, to the level of binding of the antibody specific for the 50 kD dystrophin-associated glycoprotein in a normal control cardiac tissue biopsy sample, a substantial reduction in the level of binding in the tissue, as compared to control tissue, being indicative of primary congestive cardiomyopathy.

5. A method of claim 4 wherein the mammal is a human.

6. A method of claim 5 wherein the antibody is detectable by immunofluorescence microscopy.

7. A method for screening for primary congestive cardiomyopathy in a mammal comprising the steps of:
   a) providing solubilized muscle cell extracts or membranes from the mammal;
   b) separating the components of the solubilized muscle cell membranes by gel electrophoresis;
   c) transferring the separated components from step b) to a solid support;
   d) contacting the components of the solubilized muscle cell membranes from step c) with an antibody which binds to a dystrophin-associated glycoprotein having a molecular weight of about 50 kD, under conditions appropriate for binding of the antibody to the dystrophin-associated protein;
   e) washing the components of the solubilized muscle cell membranes from step d) to remove non-specifically bound antibody;
   f) detecting the level of binding of the antibody to the 50 kD dystrophin-associated glycoprotein from the muscle cell membranes; and
   g) comparing the level of binding of the antibody to the 50 kD dystrophin-associated glycoprotein from the muscle cell to the level of binding of the antibody to the 50 kD dystrophin-associated glycoprotein from a normal control muscle cell membrane treated as in steps a) through f), a substantial reduction in the level of binding in the muscle cell membranes, as compared to control muscle cell membranes, being indicative of primary congestive cardiomyopathy.

8. A method of claim 7 wherein the muscle cell extracts or membranes are from skeletal muscle tissue.

9. A method of claim 8 wherein the mammal is a human.

10. A method of claim 7 wherein the muscle cell extracts or membranes are from cardiac muscle tissue.

* * * * *